US00PP20359P2

(12) United States Plant Patent
van Niekerk

(10) Patent No.: US PP20,359 P2
(45) Date of Patent: Sep. 29, 2009

(54) ***HEBE* PLANT NAMED 'MAGIC SUMMER'**

(50) Latin Name: *Hebe*
Varietal Denomination: Magic Summer

(75) Inventor: Johan van Niekerk, Waddinxveen (NL)

(73) Assignee: Rolini BV (I.O.), Hazerswoude (NL)

( * ) Notice: Subject to any disclaimer, the term of this patent is extended or adjusted under 35 U.S.C. 154(b) by 0 days.

(21) Appl. No.: 12/221,004

(22) Filed: Jul. 30, 2008

(51) Int. Cl.
*A01H 5/00* (2006.01)

(52) U.S. Cl. ..... Plt./226

(58) Field of Classification Search ..... Plt./226
See application file for complete search history.

*Primary Examiner*—Annette H Para
(74) *Attorney, Agent, or Firm*—Penny J. Aguirre

(57) ABSTRACT

A new cultivar of *Hebe*, 'Magic Summer', characterized by its compact growth habit, its small sized, variegated foliage with green-gray centers and white margins that is suffused with purple in cool temperatures in spring, and its free flowering habit with racemes of lavender flowers for 6 to 8 weeks in mid summer.

2 Drawing Sheets

Botanical classification: *Hebe* hybrid.
Cultivar designation: 'Magic Summer'.

BACKGROUND OF THE INVENTION

The present invention relates to a new and distinct cultivar of *Hebe*, botanically of hybrid origin and known as *Hebe* 'Magic Summer' and will be referred to hereafter by its cultivar name, 'Magic Summer'. 'Magic Summer' is grown for use as a container plant and as a landscape shrub.

The new cultivar was discovered as a chance seedling in the inventor's nursery in spring of 2004 in Waddinxveen, The Netherlands. The parentage is unknown as the inventor grows over 30 cultivars of *Hebe*. Based on foliage characteristics, it is suspected that *Hebe* 'Heartbreaker' (not patented) may be one of the parents.

Asexual reproduction of the new cultivar was first accomplished by the inventor using terminal stem cuttings in Waddinxveen, The Netherlands in 2004. It has been determined that the characteristics of this cultivar are stable and are reproduced true to type in successive generations.

SUMMARY OF THE INVENTION

The following traits have been repeatedly observed and represent the characteristics of the new cultivar, which in combination distinguish 'Magic Summer' as a new and distinct cultivar of *Hebe*.

1. 'Magic Summer' exhibits a compact growth habit.
2. 'Magic Summer' exhibits foliage that is variegated with green-gray centers and white margins that is suffused with purple in cool temperatures in spring.
3. 'Magic Summer' exhibits small leaves.
4. 'Magic Summer' is free flowering with racemes of lavender flowers in mid summer.

'Magic Summer' can be most closely compared to 'Heartbreaker' and another chance seedling discovered by the inventor 'Frozen Flame' (U.S. Plant patent application No. 12/220,988). In comparison to 'Heartbreaker', 'Magic Summer' has foliage with narrower margins and centers that are gray-green rather than green, is more compact, has smaller leaves and is more floriferous as 'Heartbreaker' rarely produces flowers. In comparison to 'Frozen Flame', 'Magic Summer' has smaller foliage, is more compact and shorter in height, is less vigorous, is more floriferous, and develops purple foliage coloration about a month later in spring.

BRIEF DESCRIPTION OF THE DRAWING

The accompanying colored photographs illustrate the overall appearance and distinct characteristics of the new *Hebe*. The photographs were taken of plants approximately six months in age as grown with 4 plugs in a 2.5-liter container outdoors in Waddinxveen, The Netherlands.

The photograph in FIG. 1 provides a side view of 'Magic Summer'.

Figure 1:
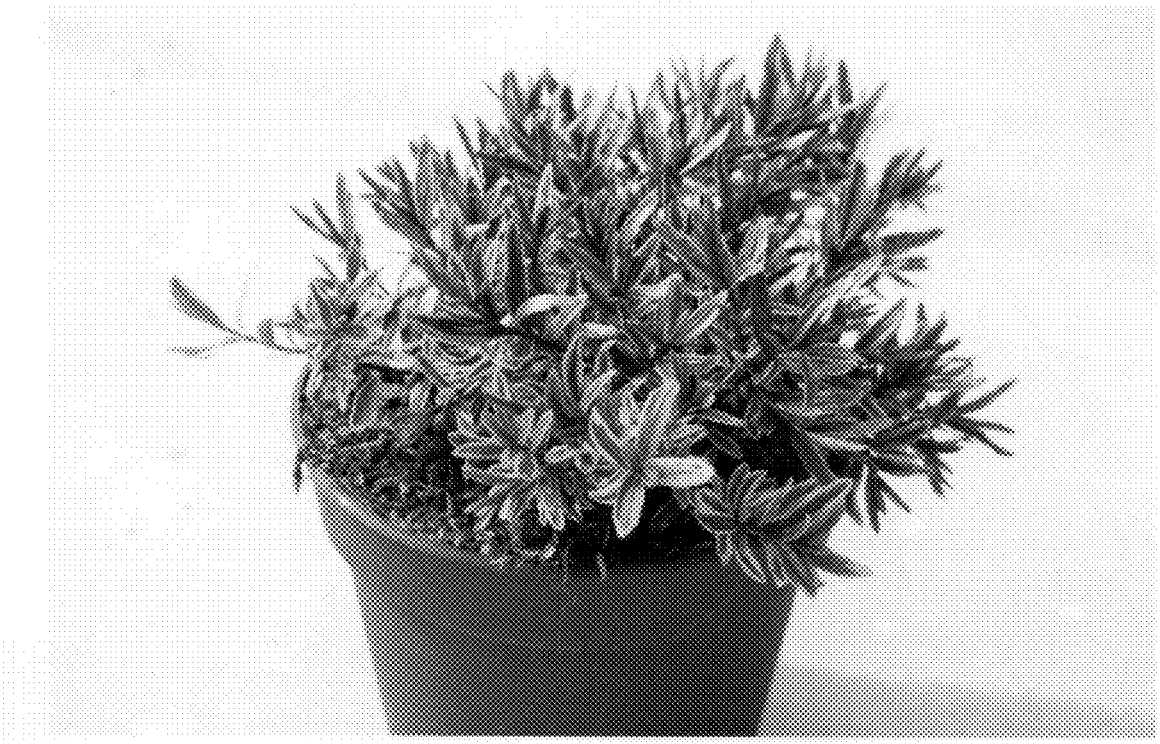
Figure 2:
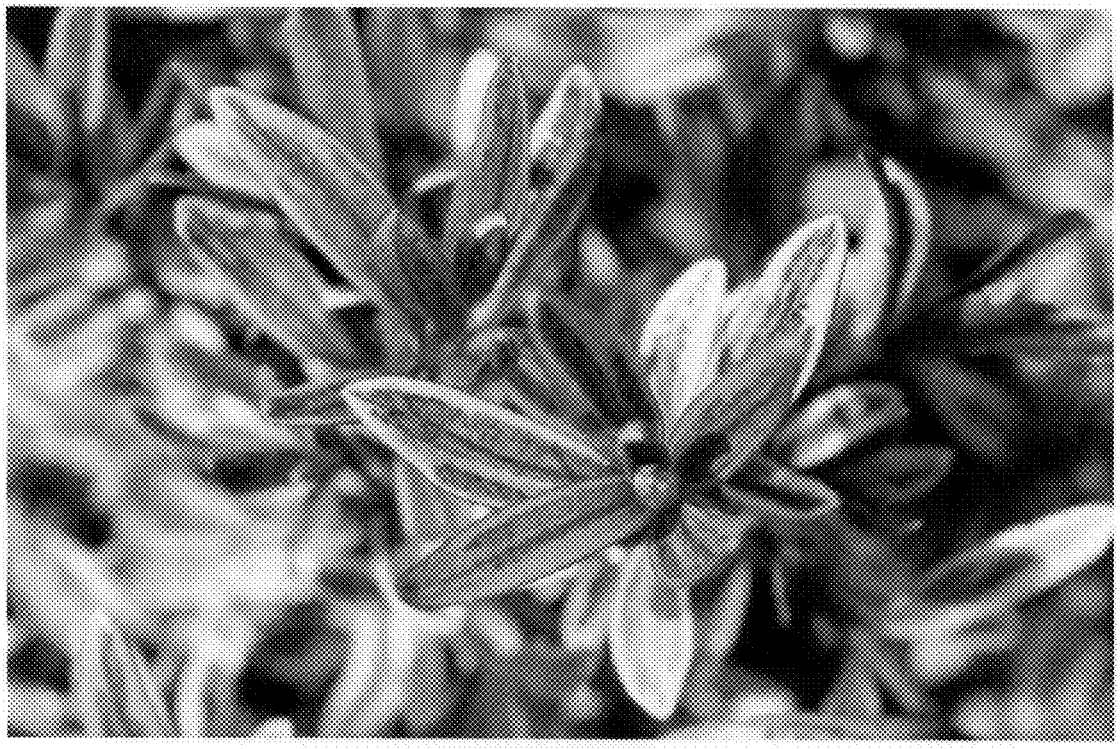

The photograph in FIG. 2 provides a close-up view of the spring foliage of 'Magic Summer'.

Figure 3:
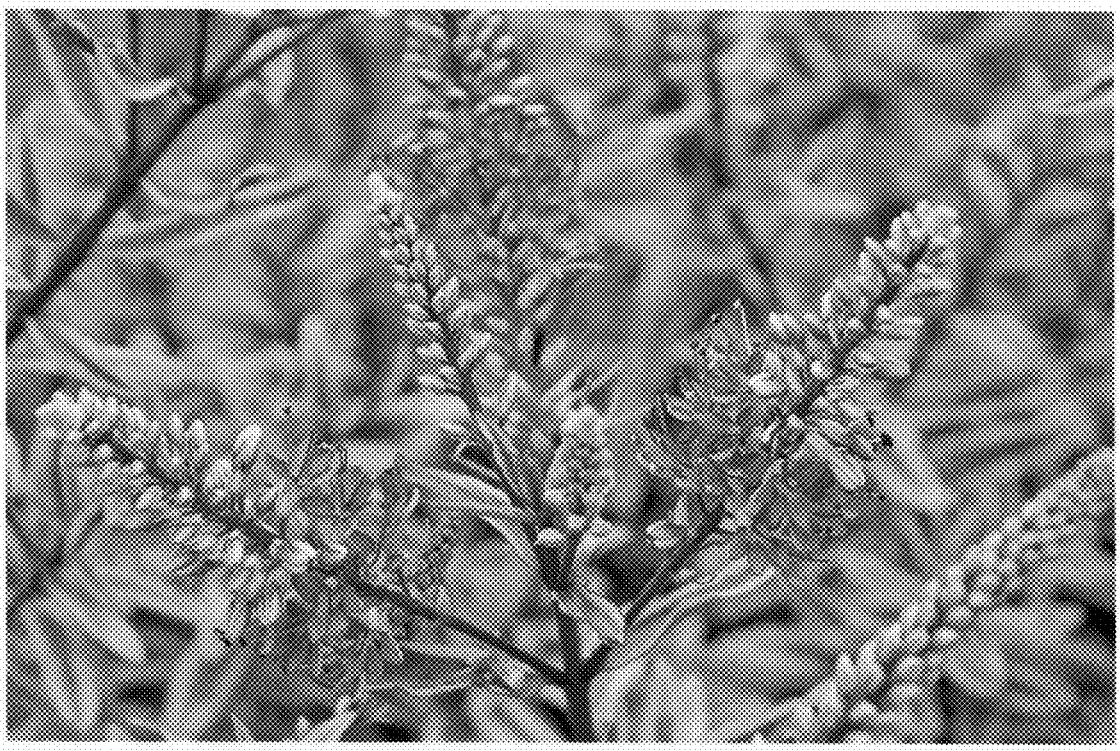

The photograph in FIG. 3 provides a close-up view of the flowers of 'Magic Summer'.

Figure 4:
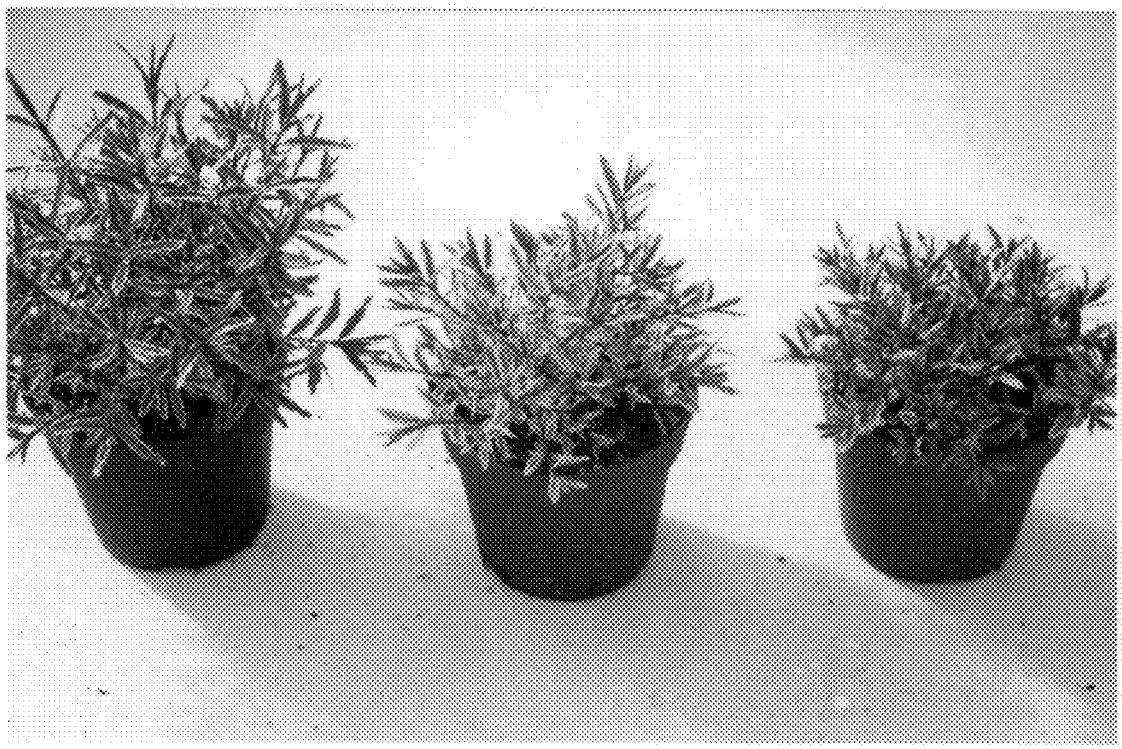

The photograph in FIG. 4 provides a comparison of 'Magic Summer' (right), 'Frozen Flame' (left), and 'Heartbreaker' (center).

The colors in the photographs are as close as possible with the photographic and printing technology utilized. The color values cited in the detailed botanical description accurately describe the colors of the new *Hebe*.

DETAILED BOTANICAL DESCRIPTION OF THE PLANT

The following is a detailed description of six month old plants of the new cultivar as grown outdoors with 4 plugs in 2.5-liter containers in Waddinxveen, The Netherlands. Plants were grown under average day temperatures of 10° to 20° C. and average night temperatures of 1° to 11° C. The phenotype of the new cultivar may vary with variations in environmental, climatic, and cultural conditions, as it has not been tested under all possible environmental conditions. The color determination is in accordance with the 2001 R.H.S. Colour Chart of The Royal Horticultural Society, London, England, except where general color terms of ordinary dictionary significance are used.

General plant characteristics:

*Plant type.*—Perennial shrub.

*Plant habit.*—Bushy, mounded, compact.

*Flowering period.*—For 6 to 8 weeks during mid summer in The Netherlands.

*Height and spread.*—Reaches about 18 cm in height and 19 cm in width in a 2.5 liter container and 40 to 60 cm in height and 80 cm in width in 3 years when grown in the garden.

*Hardiness.*—Tolerates temperatures at least from −5° C. to 35° C. and is cold hardy to at least U.S.D.A. Zone 7.

*Disease resistance.*—No particular susceptibility or resistance to diseases has been observed.

*Root description.*—Fibrous and fine.

*Growth rate.*—Moderate, about 15 cm per growth season.

*Propagation.*—Terminal stem cuttings.

Stem description:

*Stem size.*—Lateral branches are an average of 13.6 cm in length and 2.5 mm in width.

*Stem shape.*—Round.

*Stem color.*—A color between 187A and 200B.

*Stem surface.*—Glossy, covered with very short hairs.

*Internode length.*—Average of 1.2 cm.

*Branching habit.*—Freely branched from base, average of 7 lateral branches.

*Branching aspect.*—Mostly upright.

Foliage description:

*Leaf shape.*—Oblanceolate to narrow oblong.

*Leaf division.*—Simple.

*Leaf base.*—Cuneate.

*Leaf apex.*—Broadly acute.

*Leaf venation.*—Pinnate, only mid rib is conspicuous, 189A on upper surface and lower surface.

*Leaf margins.*—Entire.

*Leaf attachment.*—Sessile.

*Leaf arrangement.*—Opposite.

*Leaf surface.*—Glabrous and satiny on upper and lower surface, leathery texture.

*Leaf color.*—Upper surface summer foliage; centers 189A, margins 150D, lower surface summer foliage; centers 189A to 191A, margins 150D, winter/early spring upper surface; centers 200A, margins 186A, winter/early spring lower surface; centers 147A, margins 186A.

*Leaf number.*—Average of 24 (12 pairs) per lateral branch.

*Leaf size.*—Average of 3.1 cm in length and 8 mm in width.

*Leaf aspect.*—Held nearly horizontal to lateral branch.

*Leaf fragrance.*—None.

Flower description:

*Inflorescence type.*—Racemes of campanulate flowers, arranged at terminus and in opposite pairs at nodes.

*Inflorescence size.*—Average of 5.3 cm in length (excluding peduncle) and 2.3 cm in width.

*Flower shape.*—Campanulate.

*Flower fragrance.*—Faint, fresh, pleasant, acidic.

*Flower quantity.*—Average of 100 per raceme, average of 12 racemes in a 2.5 liter container.

*Flower arrangement.*—Packed tightly in a whorl on peduncle with flowers opening from the base towards the apex.

*Flower aspect.*—Held outward.

*Flower lastingness.*—Individual flowers last about 7 days, 20 to 30% of flowers of raceme are open at one time, self cleaning.

*Flower size.*—Average of 1 cm in depth and 8.5 mm in diameter.

*Peduncles.*—Average of 6.7 cm in length and 1 mm in width, 177A to 177B in color, surface is covered with very short hairs, round in shape, held at about a 50° angle to stem.

*Pedicels.*—Average of 1.5 mm in length and 0.5 mm in width, held at about a 45° angle to peduncle, 183B in color, surface is glabrous.

*Flower buds.*—Narrowly elliptical in shape, average of 5 mm in length and 2 mm in diameter, 90A to 90B in color blushed at apex with N155A with calyx portion 150D.

*Calyx.*—Rotate, average of 3.5 mm in length and 2 mm in width.

*Sepals.*—4, narrowly ovate in shape, margin is entire, apex is acute, base is fused on lower 30%, surface is glabrous and dull, color of upper and lower surface is 150D, average of 3.5 mm in length and 1 mm in width.

*Corolla.*—Campanulate with lower 50% of petal portion fused towards base.

*Petals.*—4, about 8 mm in length and 2.2 mm in width, lobes oblanceolate in shape, entire margins, apex of lobes obtuse, upper and lower surface is glabrous, color of upper surface when opening; N87A with throat N155A, color of lower surface when opening; N87D with fused base N155A, color of upper surface when fully open; N87A to N87B with throat N155A, color of lower surface when fully open; N87A with fused base N155A, color of both surfaces after fading; 85C.

Reproductive organs:

*Gynoecium.*—1 Pistil, stigma is clavate in shape and about 79A in color, style is about 7.8 mm in length and N78B to N78C in color, ovary is 154B to 154C in color.

*Androcoecium.*—2 stamens, anthers are elliptic in shape and dorsifixed, about 0.5 mm in length and N79A to N79B in color, filaments are about 6 mm in length and 94C to 94D in color, pollen is minimal in quantity and 4D in color.

*Fruit and seed.*—Seed production has not been observed.

It is claimed:

1. A new and distinct cultivar of *Hebe* plant named 'Magic Summer' as herein illustrated and described.

* * * * *